US009353480B2

(12) United States Patent
Benton et al.

(10) Patent No.: US 9,353,480 B2
(45) Date of Patent: May 31, 2016

(54) STERILIZABLE AND PRINTABLE NONWOVEN PACKAGING MATERIALS

(75) Inventors: Douglas McKee Benton, Northampton, MA (US); Rui Ferreira, Saint Ismier (FR)

(73) Assignee: Ahlstrom Corporation, Helsinki (FI)

(*) Notice: Subject to any disclaimer, the term of this patent is extended or adjusted under 35 U.S.C. 154(b) by 1041 days.

(21) Appl. No.: 13/444,523

(22) Filed: Apr. 11, 2012

(65) Prior Publication Data
US 2013/0269294 A1 Oct. 17, 2013

(51) Int. Cl.
*D21H 13/24* (2006.01)
*D21H 25/06* (2006.01)
(Continued)

(52) U.S. Cl.
CPC .............. *D21H 13/24* (2013.01); *B32B 5/022* (2013.01); *B32B 5/08* (2013.01); *B32B 5/26* (2013.01); *B32B 7/02* (2013.01); *D21H 13/08* (2013.01); *D21H 13/26* (2013.01); *D21H 25/06* (2013.01); *D21H 27/10* (2013.01); *D21H 27/30* (2013.01); *A61B 2017/00526* (2013.01); *A61B 2050/314* (2016.02); *A61B 2050/316* (2016.02); *A61L 2/06* (2013.01); *A61L 2/07* (2013.01); *A61L 2/206* (2013.01); *A61L 2202/181* (2013.01); *A61L 2202/24* (2013.01); *B32B 2250/02* (2013.01);
(Continued)

(58) Field of Classification Search
CPC .......................... A61B 19/026–19/0266; A61B 2019/0267–2019/027; A61B 2050/314; A61B 2050/316; D21H 13/24; D21H 25/06; D21H 27/10; D21H 27/30; D21H 13/02–13/08; D21H 13/10–13/26; B32B 2250/02; B32B 2250/20; B32B 2262/12; B32B 2307/308; B32B 2307/31; B32B 2307/54; B32B 2307/5825; B32B 2307/7145; B32B 2307/724; B32B 2439/00; B32B 2439/80; B32B 5/022; B32B 5/08; A61L 2202/181; A61L 2202/24; A61L 2/06; A61L 2/07; A61L 2/206; D04H 1/4391; D04H 3/018; D01D 5/253
USPC ........................... 442/381–393; 428/357–401
See application file for complete search history.

(56) References Cited

U.S. PATENT DOCUMENTS 5,133,835 A 7/1992 Goettmann et al.
5,387,319 A 2/1995 Mora et al.
(Continued)

FOREIGN PATENT DOCUMENTS

EP 0307173 A1 3/1989
EP 2243872 A1 10/2010
(Continued)

OTHER PUBLICATIONS

PCT International Search Report in PCT/FI2013/050356, dated Oct. 2, 2013, European Patent Office, Rijswijk.
(Continued)

*Primary Examiner* — Jennifer A Steele
(74) *Attorney, Agent, or Firm* — Ostrager Chong Flaherty & Broitman P.C.

(57) ABSTRACT

Sterilizable and printable, wet-laid non-woven substrate exhibiting high-strength and temperature resistance above 140° C., providing sufficient airflow to relieve pressure in a package formed from the substrate during sterilization, providing a significant barrier to penetration by bacteria and debris, and which is sealable to itself and to thermoplastic films, comprises blends of nanofibrillated lyocell fibers, microfibers, fibers having a flat, rectangular cross-section and binder fibers.

21 Claims, 3 Drawing Sheets

(51) Int. Cl.
    *D21H 13/26*     (2006.01)
    *D21H 27/10*     (2006.01)
    *D21H 27/30*     (2006.01)
    *D21H 13/08*     (2006.01)
    *A61B 50/30*     (2016.01)
    *A61L 2/20*     (2006.01)
    *A61L 2/06*     (2006.01)
    *A61B 17/00*     (2006.01)
    *B32B 5/26*     (2006.01)
    *B32B 5/02*     (2006.01)
    *B32B 5/08*     (2006.01)
    *B32B 7/02*     (2006.01)
    *A61L 2/07*     (2006.01)

(52) U.S. Cl.
    CPC ....... *B32B 2250/20* (2013.01); *B32B 2260/023* (2013.01); *B32B 2260/046* (2013.01); *B32B 2262/0261* (2013.01); *B32B 2262/0284* (2013.01); *B32B 2262/04* (2013.01); *B32B 2262/12* (2013.01); *B32B 2307/308* (2013.01); *B32B 2307/31* (2013.01); *B32B 2307/54* (2013.01); *B32B 2307/5825* (2013.01); *B32B 2307/7145* (2013.01); *B32B 2307/724* (2013.01); *B32B 2307/75* (2013.01); *B32B 2439/00* (2013.01); *B32B 2439/80* (2013.01); *Y10T 442/608* (2015.04); *Y10T 442/619* (2015.04); *Y10T 442/698* (2015.04)

(56) References Cited

U.S. PATENT DOCUMENTS

| | | | |
|---|---|---|---|
| 5,403,444 | A | 4/1995 | Goettmann et al. |
| 6,349,826 | B1 | 2/2002 | Kapik et al. |
| 6,352,948 | B1* | 3/2002 | Pike et al. ............ 442/384 |
| 6,808,691 | B1 | 10/2004 | Herve et al. |
| 7,758,952 | B2 | 7/2010 | Paris-Jolly et al. |
| 2005/0079093 | A1* | 4/2005 | Cannady et al. ............ 422/1 |
| 2005/0142973 | A1 | 6/2005 | Bletsos et al. |
| 2006/0068674 | A1 | 3/2006 | Dixit et al. |
| 2006/0172637 | A1 | 8/2006 | Hosokawa et al. |
| 2008/0196188 | A1* | 8/2008 | Brunner et al. ............ 15/210.1 |
| 2008/0311815 | A1 | 12/2008 | Gupta et al. |
| 2010/0272938 | A1* | 10/2010 | Mitchell et al. ............ 428/36.1 |

FOREIGN PATENT DOCUMENTS

| | | |
|---|---|---|
| WO | 9836128 A1 | 8/1998 |
| WO | 2005040495 A1 | 5/2005 |

OTHER PUBLICATIONS

PCT Written Opinion of the International Searching Authority in PCT/FI2013/050356, dated Oct. 2, 2013, European Patent Office, Rijswijk.

\* cited by examiner

STERILIZABLE AND PRINTABLE NONWOVEN PACKAGING MATERIALS

TECHNICAL FIELD

This disclosure relates to flexible and printable nonwoven substrates having high air- and steam-permeability, heat stability, and bacterial impermeability, for use in forming packages for instruments, devices, appliances and the like that require sterilization by various methods including heat, ethylene oxide and gamma radiation, and related methods of manufacture.

BACKGROUND OF INVENTION

Many types of instruments, devices, appliances and the like including, for example, surgical and other medical instruments (collectively "instruments") must be sterilized prior to use. Typically, such instruments are packaged, sealed and sterilized in disposable packaging so they can be safely transported and stored until they are used. Several sterilization techniques are known in the art, including gamma radiation, steam, dry heat and ethylene oxide sterilization techniques. In general, a sterilizing gas, vapor or liquid flows through pores in the disposable packaging and sterilizes the instruments contained therein. The sterilizing gas, vapor or liquid dissipates from the package also through the package's pores.

To form such a disposable package, an instrument may be placed between two layers of paper or plastic substrate, at least one of the layers being impervious to bacteria and debris while also being permeable to gases or steam, and the layers are sealed together to form a bag or pouch. A pouch or bag may also be formed from a paper or plastic substrate prior to inserting an instrument therein with a flap at or near an opening in the pouch such that the flap may be folded over and sealed to the pouch with an adhesive or other type of known sealing method. Alternatively, an instrument may be placed in a paper or plastic tray, sometimes molded to the shape of the instrument, and then covered and sealed with at least one layer of paper or plastic substrate that is both impervious to bacteria and debris, and permeable to gases or steam.

Substrates useful to form such packaging should exhibit sufficient airflow through the material to relieve pressure in the package during sterilization, high steam permeability, resistance to high temperatures, and should provide a significant barrier to penetration by bacteria and debris. It is also desirable that a substrate for this purpose be flexible, strong, printable, and sealable to itself and thermoplastic films and substrates. Other desired characteristics depend on the particular product disposed within the packaging.

An example of a commonly used medical packaging material is a high strength barrier nonwoven composed entirely of flash-spun polyolefin (usually high density polyethylene) sold under the trademark TYVEK® by E.I. DuPont De Nemours & Co. and described in U.S. Pat. No. 3,169,898 to Steuber. Although TYVEK® fabric is micro-porous and acts as a barrier to particulate matter that is sub-micron in size, TYVEK® fabric has very low air and gas permeability (i.e., high resistance to air and gas permeation), making the penetration of ethylene oxide and steam, and their subsequent off-gassing difficult and time consuming. TYVEK® fabric also has poor printability due to its inherent low surface energy and suppleness, and must be treated and/or coated to improve printability. Further, TYVEK® fabric has a relatively low melting point (approximately 130° C.) and will severely deform and shrink under high temperature sterilization techniques such as steam, which is typically conducted at temperatures greater than 135° C.

Barrier fabrics have been developed using wet-laid processing techniques, and often include 100% wood pulp, which is wet-laid on a Fourdrinier machine, saturated with latex and highly calendered. In the medical industry, these barrier fabrics are commonly referred to as "medical packaging paper." Wet-laid barrier fabrics made from other fibers are disclosed in U.S. Publication No. US 2010/0272938 A1, published Oct. 28, 2010. However, wet-laid nonwovens typically do not have sufficient barrier properties to prevent bacteria and debris from penetrating through the fabric, and also lack sufficient strength for packaging instruments.

Barrier properties of a porous packaging material (i.e., the ability to resist the passage of microorganisms) are measured using ASTM Standard F1608, "Standard Test Method for Microbial Ranking of Porous Packaging Materials (Exposure Chamber Method)," and result in a "Log Reduction Value" for a material. The higher the Log Reduction Value, the more effective a material is at filtering out bacteria. For example, medical grade TYVEK® fabric has a Log Reduction Value of 5. Wet-laid nonwovens and papers typically have a Log Reduction Value between 1 and 2.5. Wet-laid nonwoven fabrics containing cellulosic fibers can improve their barrier properties by using highly refined pulps, calendering and/or selecting shorter and thinner walled hardwood fibers, but these modifications also weaken the physical strength (i.e., tear strength) of the fabric, reduce opacity and increase stiffness. Cellulosic fibers also tend to weaken and discolor during certain sterilization techniques such as steam and ethylene oxide sterilization.

It is therefore an object of this disclosure to overcome the foregoing difficulties such as those associated with TYVEK® medical grade fabric and cellulosic wet-laid nonwovens and papers, and provide a nonwoven substrate that exhibits high strength and that can withstand higher temperatures than TYVEK® medical grade fabric, is steam sterilizable, has sufficient airflow to relieve pressure in the package during sterilization, provides a significant barrier to penetration by bacteria and debris, is sealable to itself and thermoplastic films and substrates, and is printable.

SUMMARY OF INVENTION

The foregoing purposes, as well as others that will be apparent, are achieved generally by providing a nonwoven substrate in the form of a wet-laid fibrous sheet comprising a low porosity top layer for barrier and printing properties and a high strength bottom layer. The top layer comprises nanofibrillated lyocell fibers. The bottom layer comprises a blend of microfibers, fibers having a flat, rectangular cross-section, binder fibers, first polymeric fibers having a first linear density and a first length and second polymeric fibers having a second linear density and a second length both greater than the first linear density and first length of the first polymeric fibers. In a preferred embodiment, the top layer further comprises microfibers; and, in another preferred embodiment, the top layer further comprises fibers having a flat, rectangular cross-section.

The fibers having a flat, rectangular cross-section are preferably splittable conjugated fibers, which have an ultra-fine structure that provides improved strength, tear resistance, and barrier properties. The splittable conjugated fibers are synthetic (preferably polyester and nylon), and are characterized by high melting points, allowing them to be sterilizable at high temperatures and, in particular, allows for steam sterilization. Preferred splittable conjugated fibers have a sectional cross-section that splits into ribbon-like fibers after fibrillation, mimicking some cellulosic fibers, and, more particularly, have a sectional cross section that is generally rectangular in shape. Such fibers are generally extruded in a cylindrical shape and split into ribbon-like fibers with varying widths and slightly curved ends.

After formation of the substrate or sheet by a wet-laid process, the sheet may be fused using a thru-air drier, an infrared drier, a gas oven, or a thermally heated calender. If a thermally heated calender is used, temperatures of approximately 150° C. and pressures of approximately 500 to 1500 pounds per square inch can sufficiently fuse the web. The advantage of a thermally heated calender to fuse the binder fibers is that it provides greater compaction of the sheet (i.e., improved barrier) compared to other methods. The fused and dried sheet is then subjected to treatment with an aqueous binder composition preferably comprising a styrenated acrylic having a glass transition temperature between 20° C. and 40° C.

Preferred blends of fibers include: (i) a bottom layer of 10 to 30% by weight of polyester microfibers, 0 to 20% by weight of splittable conjugated fibers, 5 to 15% by weight of binder fibers having a melt temperature greater than 140° C., 0 to 20% by weight of the first polymeric fiber, and 10 to 40% by weight of the second fiber; and (ii) a top layer of 40 to 80% by weight of fibrillated lyocell fibers and 20 to 60% by weight of either polyester microfiber or splittable conjugated fibers.

The nonwoven substrate may have a total weight of about 65 to about 113 grams per square meter, and should be sufficiently porous to allow the appropriate permeability to air, gas and steam while maintaining resistance to undesirable contaminants such as bacteria and debris. The average pore size of a layer or layers depends on the overall basis weight and spatial density of the substrate, the composition of fiber morphologies (shape and coarseness) making up the substrate and relative ratio of the weight of the top phase to the weight of the bottom phase, bearing in mind that the size of bacteria is generally from 0.5 to 5 micron (or micrometers, μm), and is preferably in the range of 0.25 to 11 micrometers. The average pore size may be measured using a capillary flow porometer (such as those available from Porous Materials, Inc., Ithaca, N.Y.).

Strength, porosity and permeability characteristics are imparted to the nonwoven substrates disclosed herein by the combination of synthetic fibers employed in the fiber blend. For example, the substrate has a preferred combination of properties including Gurley porosity value of at least 13 seconds per 100 milliliters and Elmendorf tear strength of greater than 400 grams in both the cross direction and machine direction. The substrate also exhibits a Log Reduction Value greater than 2 and dry process tensile strengths of at least about 10,000 grams per 25 millimeters in the machine direction and at least about 6,000 grams per 25 millimeters in the cross direction.

Preferred fiber blends maintain balance between strength, barrier properties and cost. For example, increasing the amount of lyocell fibers in the blend generally increases the resulting substrate's barrier properties, and increasing the amount of microfibers or splittable conjugated fiber in the blend generally increases the substrate's strength and dimensional stability.

Additional fibers, materials and layers may be added to the nonwoven substrate to impart other properties. Other objects, features and advantages of the present disclosure will be apparent when the detailed description of preferred embodiments is considered in conjunction with the following drawings.

DETAILED DESCRIPTION OF PREFERRED EMBODIMENTS

Figure 3A:
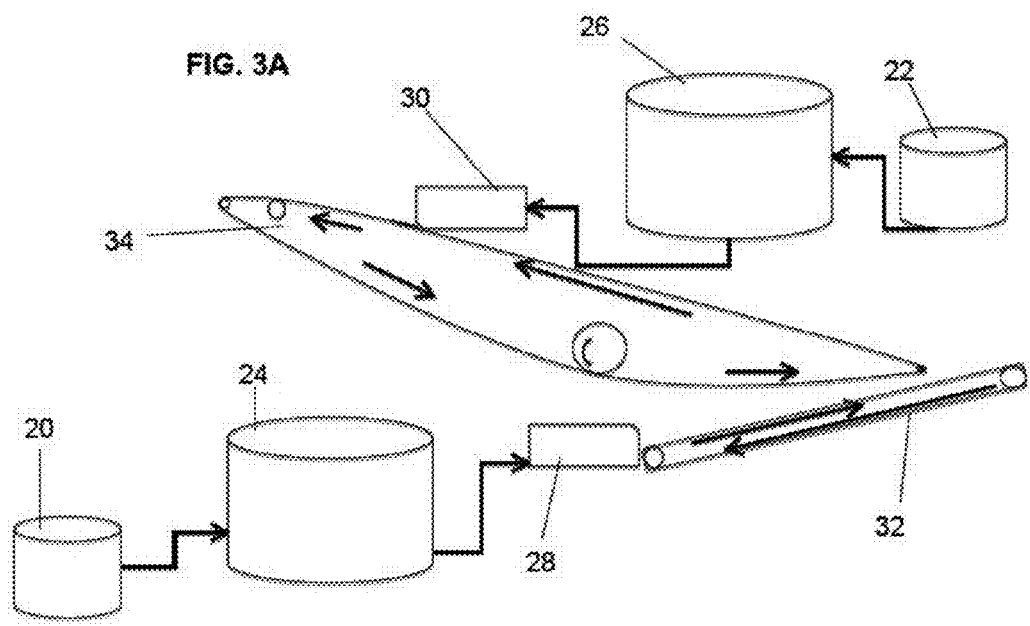
FIG. 3A is an illustration of an apparatus for forming an aqueous suspension of fibers for use in manufacturing a wet-laid nonwoven substrate.

Preferred nonwoven substrates that exhibit the desired characteristics of improved strength, bacterial barrier, tear resistance, flexibility, printability, stability during steam sterilization, air and steam permeability, heat resistance, sealability and high melting point comprise at least two layers and are produced via a wet-laid process on an inclined wire (or combination of inclined wire and Fourdrinier as in a twin wire process shown in FIG. 3A), dried and fused (optionally using a heated calender for added compaction), and treated with an aqueous binder composition. A top layer comprises nanofibrillated lyocell fibers. A bottom layer comprises a blend of microfibers, fibers having a flat, rectangular cross-section, binder fibers, first polymeric fibers having a first linear density and a first length and second polymeric fibers having a second linear density and a second length both greater than the first linear density and first length of the first polymeric fibers.

Figure 1:
FIG. 1 is a scanning electron micrograph (or SEM) of the top surface of a first embodiment of an untreated exemplary nonwoven substrate with 425 times magnification.
Figure 2:
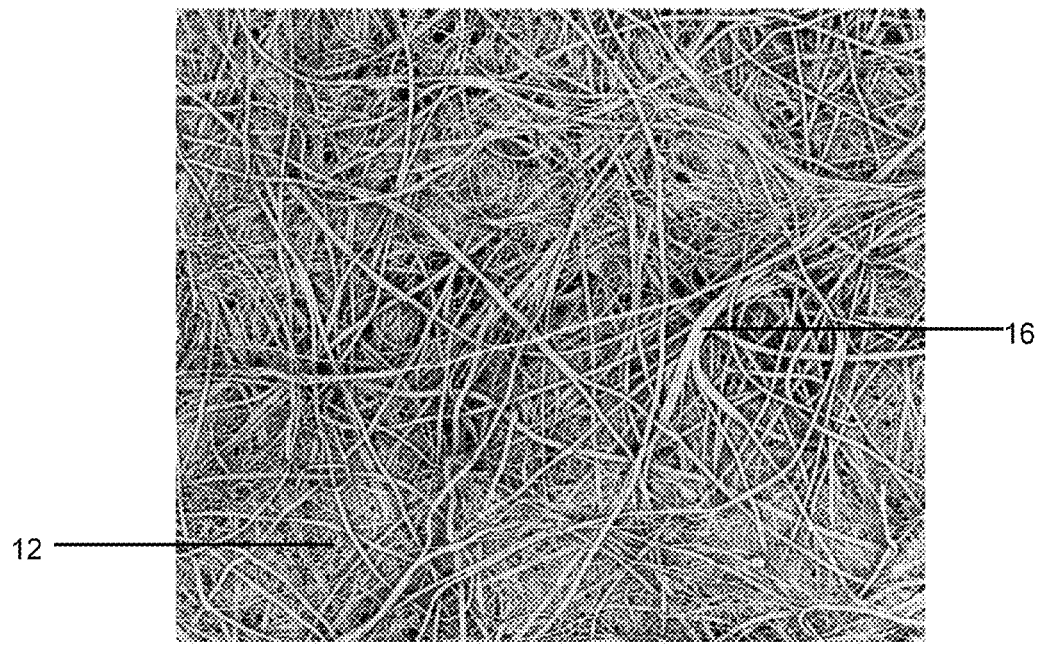
FIG. 2 is an SEM of the top surface of a second embodiment of an untreated exemplary nonwoven substrate with 385 times magnification.

The top layer further comprises either microfibers or fibers having a flat, rectangular cross-section. FIGS. 1 and 2 are SEMs of two preferred top layers of the substrate. FIG. 1 shows a top layer comprising nanofibrillated lyocell fibers 12 and fibers having a flat, rectangular cross-section 14. FIG. 2 shows a top layer comprising nanofibrillated lyocell fibers 12 and microfibers 16.

The fibers selected for use in preferred nonwoven substrates disclosed herein are synthetic fibers. As used in this application, the term "synthetic fibers" are fibers that are formed through a melt extrusion process (i.e., fiber pellets are dissolved and extruded as a continuous filament) to permit control of the length, shape and morphology of the extruded fiber. Synthetic fibers include lyocell fibers, but do not include natural cotton, wool or pulp fibers. Preferred nonwoven substrates disclosed herein comprise 100% synthetic fibers.

The diameter or linear density of a fiber may be measured in units of micron or denier per filament. The unit micron is equivalent to the unit micrometer, and represents one-millionth of a meter (or ¹⁄₁₀₀₀ of a millimeter or 0.001 mm). Denier per filament (or dpf) is the denier of a fiber divided by the number of filaments in the fiber. Denier is the weight in grams of 9,000 meters of fiber. Linear density may also be measured in Decitex (or dtex), which is the weight in grams of 10,000 meters of fiber. To convert from dtex to denier, the following formula may be used: denier=0.9×dtex. The ratio of fiber length to fiber diameter is referred to as the "aspect ratio" of the fiber.

The term "microfibers", as used herein, refers to fibers having a diameter less than 5 micron and a length of less than 3 millimeters. Preferred microfibers 16 are polyester (PET) microfibers having a non-splittable, cylindrical cross-section, and act as a processing aid in the wet-laid forming process, permitting processing of 100% synthetic compositions without specialized handling or processing equipment and also providing wet strength. A preferred microfiber 16 is a PET microfiber available from Eastman, Kingsport, Tenn., having a 2 to 4 micron (micrometer) diameter and length of about 1.5 millimeters. The Eastman PET microfibers are extruded "islands-in-the-sea" (IS) fibers made from a proprietary water dispersible polyester resin. They are available in diameters of 2 to 4 micron and can be chopped to desired length between 1.5 and 3 millimeter, and then processed to dissolve the sea portion of the fibers and leave the islands portion of the fibers.

As an alternative, polyvinyl alcohol (PVA) binder fibers can be used as a processing aid and to provide wet strength instead of the microfibers. For example, a PVA fiber available from Kuraray Co., Ltd., Osaka, Japan under the designation PV105-2 may be used to perform a similar processing function. However, use of a microfiber of similar polymer chemistry permits forming a substrate with a homogeneous fiber matrix, which may be useful for recycling at end of use.

In preferred embodiments, microfibers should be present in the bottom layer in an amount of about 10% to 30% by weight of the bottom layer. Weight measurements throughout this specification are measured in the dry state. When microfibers 16 are used in the top layer, they should be present in an amount of about 20% to 60% by weight of the top layer.

Fibers having a flat, rectangular cross-section 14 are useful in wet-laid nonwovens because their flat surfaces permit such fibers to cover holes resulting from the forming process, and thus improve barrier properties of nonwoven substrate. It has been found that increasing the amount of such flat, rectangular fibers 14 in a fabric results in increased barrier properties (relative to the use of other short cut staple fiber synthetic fibers). Preferred flat fibers are splittable conjugated fibers or standard flat polyester fibers. Conjugated fibers are those that have two different polymers within the fiber. A conjugated fiber is splittable when the two different polymers have little cohesion between the fibers. Preferred Splittable conjugated fibers 14 have a sectional cross-section that splits into multiple ribbon-like fibers (mimicking some cellulosic fibers). See FIG. 1. For example, a conjugated fiber of nylon and polyester is easily separated and useful in the preferred nonwoven substrates. Such splittable conjugated fibers have an ultrafine structure that, after fibrillation, provides good barrier properties similar to refined pulp, but also imparts improved strength, dimensional stability, and good drainage. Fibrillation of the splittable conjugated fiber occurs during the wet-laid process from shearing forces resulting from the mechanical action (or turbulence) under dilute conditions, which are sufficient to spontaneously split the conjugate fibers during the wet-laid process.

In preferred embodiments, conjugated fibers 14 should be present in the bottom layer in an amount of about 0% to 20% by weight of the bottom layer. When conjugated fibers 14 are used in the top layer, they should be present in an amount of about 20% to 60% by weight of the top layer.

A preferred conjugated polyester/nylon short-cut fiber is available from Kuraray Co., Ltd., Osaka, Japan under the trade name WRAMP, Solid Core Type, which has a linear density of 3.3 dtex (2.97 denier) before split and length of 3-10 millimeters. The linear density after split is approximately 0.3 dtex (0.27 denier). The WRAMP fiber has a split number of 11 (6 polyester/5 nylon). WRAMP fibers provide substrates with high tear factor, low air permeability, smaller pore size, high luster and high folding capacity. Kuraray WRAMP splittable conjugated fibers also have a high melting temperature, which makes them steam sterilizable.

Binder fibers useful in the bottom layer should have a high melting temperature, 140° C. or higher, and may be formed from polyacrylate, styrene-butadiene copolymer, polyvinyl chloride, ethylene-acrylate copolymer, vinyl acetate-acrylate copolymer and coPET binders. Preferred binder fibers are bi-component fibers of the type having an outer sheath and a core. An example of such a bi-component binder fiber is the high temperature copolyester binder fibers (copolyester/polyester), Type TJ04BN supplied by Teijin Fibers Limited, Osaka, Japan having linear density of 1.7-3 dtex (1.53-2.7 denier), length of 5-15 millimeters, and sheath melting temperature of about 150° C. Other examples of binder fibers that may be used include Type 7080 crystalline bicomponent coPET/PET fibers, available from Unitika Fibers Ltd., Osaka, Japan, having a linear density of 2.0 denier, a length of 5 mm and a sheath melt temperature of 160° C.) and Kuraray Type N720H (melting temperature 150° C.). In preferred embodiments, binder fibers should be present in the bottom layer in an amount of about 5% to 15% by weight (in dry state) of the bottom layer.

Preferred nanonfibrillated lyocell fibers 12 used in the substrate are fibers formed by dissolving and extruding naturally occurring cellulosic materials, such that the chemical nature of the naturally occurring cellulosic material is retained after the fiber formation process, and the length, diameter and morphology of the extruded fiber may be controlled. Therefore, preferred lyocell fibers are synthetic fibers as defined herein.

During fiber formation, lyocell fibers 12 typically fibrillate, or form micro-fibrils or nano-fibrils on the fiber surface, and fill in gaps in the top layer left by the conjugated fibers 14 or microfibers 16 during wet-laid processing, as shown in FIGS. 1 and 2. A preferred lyocell fiber is a nano-fibrillated fiber available from Engineered Fibers Technology in Longmeadow, Mass. under the trademark EFTec 010-4. Other nano-fibrillated lyocell fibers may also be used. In preferred embodiments, lyocell fibers 12 should be present in the top layer in an amount of about 40% to 80% by weight of the top layer.

The remaining fibers in the fiber blend of the bottom layer are preferably polymeric fibers of varying linear density and length. For example, a first fiber may be a short-cut polyester fiber having a liner density of 1.7 dtex (1.53 denier) and a length of about 5-15 mm, such as a 10 millimeter 100% Post Consumer recycled polyester fiber ("EcoPET") from Teijin Fibers Limited, Type TA4 may be used, or alternatively a 10 millimeter Kuraray EP303, or Teijin's virgin 10 mm TA04N fiber may be used. Such a fiber may be present in the amount of about 0% to 20% of the bottom layer. A second polymeric fiber used in the bottom layer may be a standard polyester fiber having a linear density of 1.5-6.0 dtex (1.35-5.4 denier) and length of 15-25 millimeters. For example, a polyester fiber from William Barnet & Sons, LLC, Product No. P50FM may be used (a High Tenacity fiber 5.2 dtex/19 millimeter). Such a fiber may be present in the amount of about 10% to 40% of the bottom layer.

The weight of the top layer is preferably in the range of about 10 to 25 grams per square meter, and the weight of the bottom layer is preferably in the range of about 40 to 60 grams per square meter. The bottom layer is typically heavier than the top layer by about 2 to 3 times. Preferably, the weight ratio of top layer to bottom layer is about 1 to 2.5. A higher weight ratio of top layer to bottom layer, or using a more massive top layer for a given bottom layer, will produce a more closed and higher barrier substrate. If the weight ratio of top layer to bottom layer is changed, without changing the total basis weight of the combined layers, increasing the ratio will decrease the strength of the substrate and improve barrier properties. To increase strength properties, the weight of the bottom layer should be increased.

A first exemplary fiber blend for a two-layer nonwoven substrate in accordance with the foregoing disclosure is set forth in TABLE I, and referred to herein as Example 1.

TABLE I

Fiber Composition of Two-Layer Structure - 10242011-1B

| Component | Brand | Diameter or Linear Density | Length (mm) | Weight (%) | Aspect Ratio (L/D) |
|---|---|---|---|---|---|
| TOP LAYER (Weight - 20 gsm): | | | | | |
| PET/Nylon Conjugated Fiber | Kuraray WRAMP | 3.3 dtex (2.97 denier) (before split) | 5 | 40 | 893 |
| Fibrillated Lyocell | EFTec 010-04 | nanofibrillated | 4 | 60 | |
| BOTTOM LAYER (Weight - 44 gsm): | | | | | |
| PET Microfiber | Eastman Microfiber | 1.5 micron | 1.5 | 20 | 1000 |
| PET/Nylon Conjugated Fiber | Kuraray WRAMP | 3.3 dtex (2.97 denier) (before split) | 5 | 10 | 893 |
| CoPET/PET Binder Fiber | Teijin TJ04BN | 2.2 dtex (1.98 denier) | 5 | 10 | 357 |
| Polyester Fiber | Teijin TA4 | 1.7 dtex (1.53 denier) | 10 | 20 | 12000 |
| Polyester Fiber | Barnet P50FM - High tenacity | 5.2 denier | 19 | 40 | 712 |

A second exemplary fiber blend is set forth in TABLE II, and referred to herein as Example 2.

TABLE II

Fiber Composition of Two-Layer Structure - 10242011-2B

| Component | Brand | Diameter or Linear Density | Length (mm) | Weight (%) | Aspect Ratio (L/D) |
|---|---|---|---|---|---|
| TOP LAYER (Weight - 20 gsm): | | | | | |
| PET Microfiber | Eastman Microfiber | 1.5 micron | 1.5 | 40 | 1000 |
| Fibrillated Lyocell | EFTec 010-04 | | 4 | 60 | |
| BOTTOM LAYER (Weight - 44 gsm): | | | | | |
| PET Microfiber | Eastman Microfiber | 1.5 micron | 1.5 | 20 | 1000 |
| PET/Nylon Conjugated Fiber | Kuraray WRAMP | 3.3 dtex (2.97 denier) (before split) | 5 | 10 | 893 |
| CoPET/PET Binder Fiber | Teijin TJ04BN | 2.2 dtex (1.98 denier) | 5 | 10 | 357 |
| Polyester Fiber | Teijin TA4 | 1.7 dtex (1.53 denier) | 10 | 20 | 12000 |
| Polyester Fiber | Barnet P50FM - High tenacity | 5.2 denier | 19 | 40 | 712 |

The specific ratio of fibers in the fiber blends of preferred nonwoven substrates varies depending on what specific material properties are required. Employing the appropriate mix of synthetic fibers permits tuning the fiber matrix to the desired porosity and barrier characteristics, while taking into account cost considerations. In general, a double layer substrate is more cost effective because it allows a thinner, but higher concentration of fine fibers (higher barrier) within a layer, thus using fewer specialty fibers. If a high barrier property is required (i.e., bacterial barrier), greater amounts of lyocell fibers should be used, while substituting conjugate or microfiber fibers for lyocell fibers will render a slightly more porous sheet. However, too much lyocell makes it difficult for water to drain from the substrate during production and will require slower production speeds. Tuning the amount of lyocell fibers within the ranges set forth in this application will prevent this problem, and represents a level of good runnability (i.e., faster processing speeds and fewer breaks) and performance.

If the nonwoven substrate is produced in a two-layer structure, one layer can be designed specifically for barrier properties and the other layer can be designed to provide strength. This type of construction permits one to minimize fiber costs.

Although preferred embodiments are described as a double-layer construction, the nonwoven substrate is not limited to the use of only two layers. The grammage and characteristics of the various sheets may be adjusted according to the general teachings of the present disclosure. For example, a three-layer substrate may be formed having a high barrier central layer that is not as strong and two outer layers that exhibit strength, or a high barrier central layer may be sandwiched between an outer layer with good sealing properties and an outer layer with high printability.

Nonwoven substrates that exhibit the desired characteristics of improved strength, bacterial barrier, tear resistance, flexibility, printability, stability during steam sterilization, air (and steam) permeability, heat resistance, sealability and high melting point, may be produced by conventional wet-laid processes, preferably using an inclined wire machine.

Figure 3B:
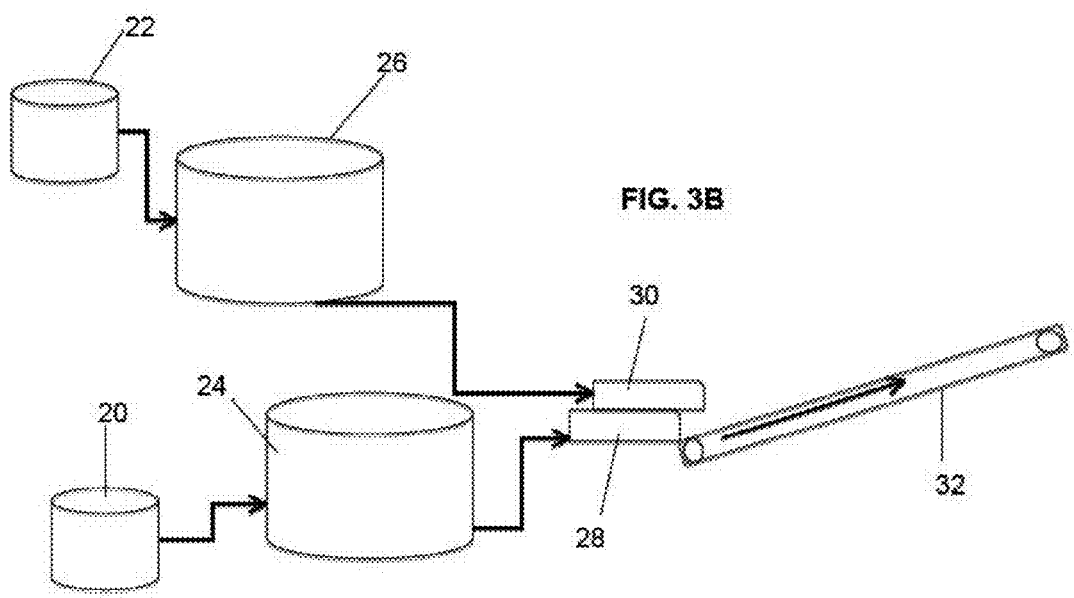
FIG. 3B is an illustration of an alternative apparatus for forming an aqueous suspension of fibers for use in manufacturing a wet-laid nonwoven substrate.

Referring to FIGS. 3A and 3B, at least two suspensions of fibers are prepared by filling hydropulpers 20, 22 with warm water, agitating the water, adding a blend of fibers as set forth above, and further agitating the mixture for approximately 2 to 20 minutes to mix the fibers and create a fiber slurry. For example, the fibers used for bottom layer are mixed in hydropulper 20 and the fibers used for the top layer are mixed in hydropulper 22. Each of the fiber slurries is then transported to a mixing chest 24, 26 to further mix the fibers of each blend, and then to a blending chest to dilute the fiber slurry to the desired consistency of 0.2% to 0.4%. Fibrillation of the splittable conjugated fiber occurs in this part of the wet-laid process. The hydropulpers 20, 22 and mixing chests 24, 26 apply sufficient shearing forces resulting from the mechanical action (or turbulence) under dilute conditions to spontaneously split the conjugate fibers. Heating the water to about 40-80° C. and/or hydroentanglement may also aid in splitting the fibers, but are not necessary.

When the fiber slurries are sufficiently mixed and diluted, each of fiber slurries is transported to a headbox 28, 30 for delivery to the web-forming machine, where the fiber slurries are dewatered on an inclined wire forming line 32 to form a multi-layer sheet. Referring to FIG. 3A, the top layer may be formed on a separate wire 34 (which, in this twin wire configuration, could alternatively be a Fourdrinier style former), and then placed on top of the bottom layer while the bottom layer is traveling up the inclined wire forming line 32. Alternatively, the bottom layer and top layer may be placed onto the inclined wire forming line 32 successively, as shown in FIG. 3B. Thus, each layer may be formed separately on a wire and then combined to form the substrate, or the bottom layer may be formed on the wire, and the top layer may be formed directly on the bottom layer.

Figure 4A:
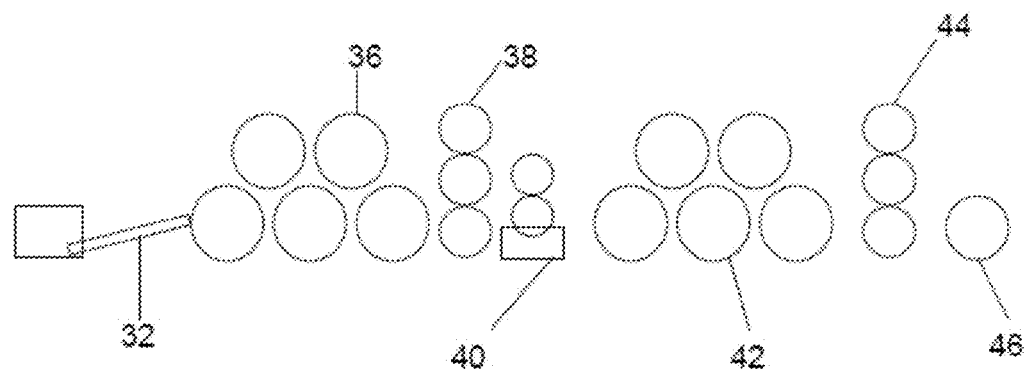
FIG. 4A is an illustration of an apparatus for manufacturing a wet-laid nonwoven substrate.
Figure 4B:
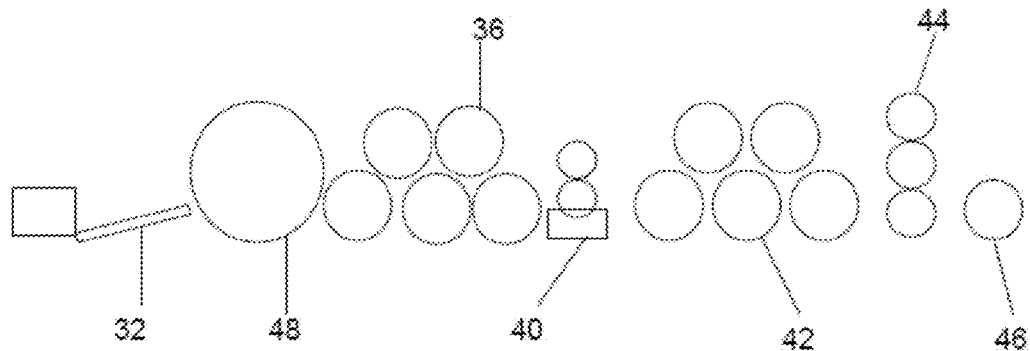
FIG. 4B is an illustration of an alternative apparatus for manufacturing a wet-laid nonwoven substrate.

After the substrate is formed from the fiber blends, the formed sheet may be dried and fused as shown, for example, in the process lines of FIGS. 4A and 4B. FIG. 4A shows a process of using a heated calendering step for fusing and consolidation. FIG. 4B shows a process of using a thru air drier 48 for fusing the binder fibers instead of the heated precalender 38 shown in FIG. 4A. Other means of fusing the fibers may also be used, such as infrared, or gas ovens.

In the case of FIG. 4A, a calendering process may be introduced to fuse the sheath of the bicomponent binder fibers to the other synthetic fibers, to render the surface smooth, decrease its permeability (via densification) to the desired target, and achieve a porosity value lower than 20 L/min/100 cm$^2$ as measured by the testing method described in TAPPI T251 (before treatment). This test measures the air permeability of a square centimeter of fabric, or the volume of air that flows through the fabric per minute. The calender section may have single or multiple nip configurations for web consolidation. Calendering may be done on-line or off-line, but it is preferable to have it in-line. The calendering process should minimize any disruption or degradation of the bottom surface of the bottom layer. This can be accomplished by exposing only the top of the sheet to heat and pressure, and the bottom of the sheet only to pressure. For example, a heated steel roll and a non-heated rubber lower roll can be employed. Preferred calendering pressures vary between 300 and 2,000 pounds per square inch, preferably 500-1,500 pounds per square inch. Preferred temperatures of the top roll vary between 250-350° F., preferably 295° F., depending on the type of fibers that are used in the fiber blend.

Referring to FIG. 4A, the formed substrate sheets may be transferred from the inclined wire forming line 32 to a first drying section comprising a series of drying cans 36 to remove water. Then, the formed substrate sheets may be transferred to a heated precalender section 38 for fusing the binder fiber.

Various binders may then be applied to the formed sheet in aqueous form to further improve strength and barrier properties. The aqueous binder treatment is preferably applied after calendering the sheet, and may be provided on-line or off-line, to further enhance final product properties, such as increasing the density of the sheet, developing inter-fiber bonding and strength. A saturating size press 40 or other conventional means may be used to apply the binder.

Acceptable aqueous binders include, but are not limited to: styrenated acrylic (for example, BASF nx-4787), coPET (for example, Eastman 1200), acrylic (for example, Eco 100 Dow), polyurethane (for example, Permax 202), styrene-butadiene copolymer (for example, GenFlo 3060), acrylic copolymer (for example, BASF 4612), or combination there of (either sequentially added to the web or as a single mixture). The binder should have a glass transition temperature in the range of about +20° C. to +40° C. The aqueous binder is used in combination with the binder fibers to develop inter-fiber bonding and strength. Additionally, the aqueous binder boosts strength and ties down the fibers to limit the amount of fibers raised above the surface of the substrate.

The aqueous binder may be applied as an add-on to the substrate in an amount equal to about 15 to 28 grams per square meter. In the exemplary embodiments shown above, about 18 grams per square meter of aqueous binder were applied, but the application amount could range from between 15% to 36% add-on depending on the basis weight of each layer of the substrate. The total weight of the nonwoven substrates in this disclosure, including the aqueous binder treatment, will be about 65 to about 113 grams per square meter Water may then be removed from the calendered sheet by passing the sheet through a second drying section 42 comprising drying cans or a through-air dryer to permit the aqueous binder treatment to cure. Additional soft calendering 44 may be applied to further smooth the surface, decrease its permeability (via densification) to the desired target, and achieve a porosity value of less than 5 L/min/100 cm$^2$ as measured by the testing method described in TAPPI T251 (after treatment). This test measures the air permeability of a square centimeter of fabric, or the volume of air that flows through the fabric per minute. The calender section may have a single or multiple nip configurations for web consolidation. Calendering may be done on or off-line, but it is preferable to have it in-line. The post calendering process should again minimize any disruption or degradation of the bottom surface of the bottom layer fiber matrix. This can be accomplished by exposing only the top of the sheet to heat and pressure, and the bottom of the sheet only to pressure. For example, a heated steel roll and a non-heated rubber lower roll can be employed. Preferred calendering pressures vary between 300 and 1,500 pounds per square inch, preferably 500-1,000 pounds per square inch. Preferred temperatures of the top roll vary between 200-300° F., preferably 250° F., depending on the type of binder(s) used in the aqueous binder treatment.

Post treatment soft calendering is beneficial, but is not required. The calendered substrates may then be further processed (for example, slitting) and wound to a roll in the rewind section 46.

In an alternative process shown in FIG. 4B, a thru air drier 48 may be used for fusing the binder fibers instead of the heated precalender 38 shown in FIG. 4A. In this embodiment, the binder fibers in the formed substrate sheets are fused and the sheets are then dewatered in the first drying section 36. One advantage of this process is that it is immediately adaptable to production lines (inclined wire) currently using through-air dryers, infrared, or gas ovens for binder fiber fusing. Most production lines do not use thermal calendering for fusing or densification purposes.

The nonwoven substrates described above exhibit improved porosity, strength and barrier properties as compared to TYVEK® and commercially available wet-laid medical papers. For example, preferred substrates have a Log Reduction Value of 2 or greater, as measured in accordance with ASTM Standard F1608, but also have improved airflow permeation resistance and strength. Airflow permeation resistance is measured by a Gurley densometer in accordance with TAPPI T460 standard test method, and measures the amount of time it takes (in seconds) for 100 milliliters of air to pass through a sample. For barrier applications, it is better for airflow permeation resistance to be higher. Elmendorf tear strength measures the force it takes to tear a 4 by 2 inch sample of a material in grams in accordance with TAPPI T414 standard test method. Higher values represent stronger substrates. Nonwoven substrates according the present disclosure have an airflow permeation resistance of at least 13 seconds per 100 milliliters and Elmendorf tear strength of at least 400 grams in both machine direction and cross direction. Preferred substrates also have a dry process tensile strength of at least about 10,000 grams per 25 meters in the machine direction and at least about 6,000 grams per 25 millimeters in the cross direction, as measured by TAPPI T494 standard test method.

The nonwoven substrates disclosed herein are also able to withstand higher temperatures than TYVEK® and are more durable than conventional medical packaging paper, such as the medical packaging paper available from Kimberly Clark as 52# Medical Packaging Paper, Type S-60857 ("KC S-60857"). The physical properties of Examples 1 and 2 compared to similar physical properties of TYVEK® and KC S-60857 are shown in Table III.

TABLE III

Physical Properties

| Properties | Units | Test Method | Example 1 | Example 2 | TYVEK® 1074B | KC S-60857 |
|---|---|---|---|---|---|---|
| Basis Weight | g/m² | | 82.3 | 83.5 | 74 | 85 |
| Ta2 Thickness | Microns | TAPPI T411 | 220 | 203 | 185 | 105 |
| Airflow Permeation Resistance | S/100 ml | TAPPI T460 (Gurley Densometer) | 13 | 20 | 22 | 7 |
| MD Dry Tensile Strength | g/25 mm | TAPPI T494 | 12000 | 12500 | 12500 | 12000 |
| CD Dry Tensile Strength | g/25 mm | TAPPI T494 | 7800 | 7600 | 14200 | 9000 |
| MD Elmendorf Tear Strength | g | TAPPI T414 | 723 | 712 | 380 | 100 |
| CD Elmendorf Tear Strength | g | TAPPI T414 | 650 | 646 | 430 | 150 |
| MD Elongation | % | TAPPI T494 | 19 | 18 | 24 | 8 |
| CD Elongation | % | TAPPI T494 | 18 | 18 | 26 | 12 |
| LRV | Log | ASTM F1608 | 2.9 | N/A | 5.3 | 2 |

Tests of the porosity of the top layer of Examples 1 and 2 prior to calendering show that greater than 17 liters of air flow through a square centimeter sample of the top layers per minute, as measured by the standard test method of TAPPI T251. The top layer in Example 1 has a porosity of 17.7 l/m/100 cm2 and the top layer in Example 2 has a porosity of 20.7 l/m/100 cm2 (untreated). This shows that the top layers provide good barrier properties even without binder treatment.

The data shows that nonwoven substrates manufactured as set forth herein are steam sterilizable and sufficiently porous to allow gases to escape, while providing adequate bacterial protection and strength. In addition to the foregoing properties, because the nonwoven substrates do not include any wood pulp, the substrates will not yellow during sterilization or ultraviolet exposure. The substrates also have good uniformity and are printable via flexographic, lithographic, offset and gravure printing methods without the need for expensive ink drying accelerants to cure the ink onto the surface. It is believed this results from the use of fibers that have inherently higher surface energy than high-density polyethylene used in TYVEK® products.

The above disclosure, embodiments and examples are illustrative only and should not be interpreted as limiting. Modifications and other embodiments will be apparent to those skilled in the art, and all such modifications and other embodiments are intended to be within the scope of the present invention as defined by the claims.

We claim:

1. A multi-layer non-woven sterilizable packaging material comprising:
   a top layer comprising nanofibrillated lyocell fibers; and
   a bottom layer comprising a blend of:
   (a) microfibers;
   (b) synthetic fibers having a flat, generally rectangular cross-section with at least one dimension that is generally flat and a length of about 5 to 10 millimeters, the synthetic fibers having a flat, generally rectangular cross-section are ribbon-like fibers that have split apart from splittable conjugated fibers, the splittable conjugated fibers comprising a PET component and a Nylon component, such that a first of the ribbon-like fibers that have split apart from the splittable conjugated fibers consists of the PET component and a second of the ribbon-like fibers that have split apart from the splittable conjugated fibers consists of the Nylon component;
   (c) binder fibers;
   (d) a first polymeric fiber having a first linear density and a first length; and
   (e) a second polymeric fiber having a second linear density and a second length both greater than the first linear density and first length of the first polymeric fiber;
   the packaging material having a Log Reduction Value greater than 2.

2. The packaging material of claim 1, wherein the top layer further comprises fibers selected from the group consisting of the synthetic fibers having a flat, generally rectangular cross-section and the microfibers.

3. The packaging material of claim 2, wherein the lyocell fibers comprise about 40 to 80% by weight of the top layer.

4. The packaging material of claim 3, wherein the blend of fibers in the bottom layer comprises:
   (a) 10 to 30% by weight of said microfibers;
   (b) 10 to 20% by weight of said synthetic fibers having a flat, generally rectangular cross-section; and
   (c) 5 to 15% by weight of said binder fibers.

5. The packaging material of claim 2, wherein said microfibers comprise polyester.

6. The packaging material of claim 1, wherein said binder fibers comprise coPET/PET bicomponent binder fibers having a melting point of greater than 140° C.

7. The packaging material of claim 1, wherein the first and second polymeric fibers comprise polyester, the first length of the first polymeric fiber is about 3 to 10 millimeters and the second length of the second polymeric fiber is about 5 to 20 millimeters.

8. The packaging material of claim 1, wherein the binder fibers have a length of about 5 to 10 millimeters.

9. The packaging material according to claim 1, wherein said packaging material comprises pores having an average pore size of about 0.25 to 11 micrometers.

10. The packaging material according to claim 7, further comprising a binder treatment dispersed onto the packaging material, the binder treatment selected from the group consisting of styrenated acrylic, copolyester, acrylic, polyurethane, styrene butadiene and acrylic copolymer.

11. The packaging material according to claim 10, wherein the binder treatment has a weight of about 15% to 36% of the weight of the packaging material.

12. The packaging material according to claim 1 having a total weight of about 65 to about 113 grams per square meter.

13. The packaging material according to claim 2, wherein the packaging material has airflow permeation resistance of least 13 seconds per 100 milliliters and Elmendorf tear strength of at least 400 grams in both machine direction and cross direction.

14. The packaging material according to claim 1, wherein the packaging material has a dry process tensile strength of at least about 10,000 grams per 25 meters in the machine direction and at least about 6,000 grams per 25 millimeters in the cross direction.

15. A package for an article comprising the packaging material of claim 1.

16. The packaging material of claim 1, wherein the bottom layer has a bottom layer weight that is about 2 to 3 times a top layer weight of the top layer.

17. The packaging material of claim 16, wherein the top layer weight is in the range of about 10 to 25 grams per square meter.

18. The packaging material of claim 17, wherein the bottom layer weight is in the range of about 40 to 60 grams per square meter.

19. The packaging material of claim 1, wherein the synthetic fibers having a flat, generally rectangular cross-section further comprise curved ends.

20. A multi-layer non-woven sterilizable packaging material comprising:
 a top layer comprising nanofibrillated lyocell fibers; and
 a bottom layer having a bottom layer weight that is about 2 to 3 times a top layer weight of the top layer, the bottom layer comprising a blend of:
 (a) microfibers;
 (b) synthetic fibers having a flat, generally rectangular cross-section with at least one dimension that is generally flat and comprising ribbon-like fibers that have split apart from splittable conjugated fibers, the synthetic fibers having a flat, generally rectangular cross-section are ribbon-like fibers that have split apart from splittable conjugated fibers, the splittable conjugated fibers comprising a PET component and a Nylon component, such that a first of the ribbon-like fibers that have split apart from the splittable conjugated fibers consists of the PET component and a second of the ribbon-like fibers that have split apart from the splittable conjugated fibers consists of the Nylon component;
 (c) binder fibers;
 (d) a first polymeric fiber having a first linear density and a first length; and
 (e) a second polymeric fiber having a second linear density and a second length both greater than the first linear density and first length of the first polymeric fiber,
 the packaging material having a dry process tensile strength of at least about 10,000 grams per 25 meters in the machine direction and at least about 6,000 grams per 25 millimeters in the cross direction.

21. The packaging material of claim 20, wherein the synthetic fibers having a flat, generally rectangular cross-section and curved ends have a length of about 5 to 10 millimeters.

\* \* \* \* \*